United States Patent
Reiffen et al.

(10) Patent No.: US 8,445,219 B2
(45) Date of Patent: May 21, 2013

(54) METHOD OF DETERMINATION OF RECEPTOR BINDING SATURATION EFFECTED BY MONOCLONAL ANTIBODIES

(75) Inventors: Karl-August Reiffen, Muehltal (DE); Oliver Rosen, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 373 days.

(21) Appl. No.: 13/055,567

(22) PCT Filed: Jun. 26, 2009

(86) PCT No.: PCT/EP2009/004615
§ 371 (c)(1),
(2), (4) Date: Jan. 24, 2011

(87) PCT Pub. No.: WO2010/009794
PCT Pub. Date: Jan. 28, 2010

(65) Prior Publication Data
US 2011/0136150 A1      Jun. 9, 2011

(30) Foreign Application Priority Data
Jul. 25, 2008   (EP) ..................... 08013415

(51) Int. Cl.
*G01N 31/00*   (2006.01)
*G01N 33/53*   (2006.01)

(52) U.S. Cl.
USPC ........... 435/7.21; 435/7.1; 436/501; 436/518; 424/9.1; 424/520; 422/430; 530/300; 530/350

(58) Field of Classification Search
None
See application file for complete search history.

(56) References Cited

U.S. PATENT DOCUMENTS
2007/0172895 A1    7/2007   Fleener et al.

FOREIGN PATENT DOCUMENTS
FR          2764388 A1    12/1998

OTHER PUBLICATIONS

International Search Report for PCT/EP2009/004615, mailed Sep. 2, 2009, 4 pages.
Perez-Soler et al. (1994) "Tumor epidermal growth factor receptor studies in patients with non-small-cell lung cancer of head and neck cancer treated with monoclonal antibody RG 83852," *Journal of Clinical Oncology* 12(4):730-739.
Sihra et al. (1997) "Expression of high-affinity IgE receptors (FcεRI) on peripheral blood basophils, monocytes, and eosinophils in atopic and nonatopic subjects: Relationship to total serum IgE concentrations," *Journal of Allergy and Clinical Immunology* 99(5):699-706.
Townsend et al. (2006) "Development of a Whole Blood CD86 Receptor Competition Assay to Measure Receptor Saturation by Belatacept," *Americal Journal of Transplantation* 6(2):698, Abstract.
Woska et al. (2003) "Small molecule LFA-1 antagonists compete with an anti-LFA-1 monoclonal antibody for binding to the CD11a I domain: development of a flow-cytometry-based receptor occupancy assay," *Journal of Immunological Methods* 277:101-115.

*Primary Examiner* — Lisa Cook
(74) *Attorney, Agent, or Firm* — Goodwin Procter LLP

(57) ABSTRACT

The invention relates to the determination of the degree of membrane receptor binding by specific monoclonal antibodies. This method is notably beneficial for monoclonal antibodies that are used in targeted therapies in order to define a target effective dose (TED). Especially the invention relates to the determination of the saturation degree of receptor binding effected by an anti-EGFR antibody of interest.

17 Claims, 1 Drawing Sheet

Figure 1A:
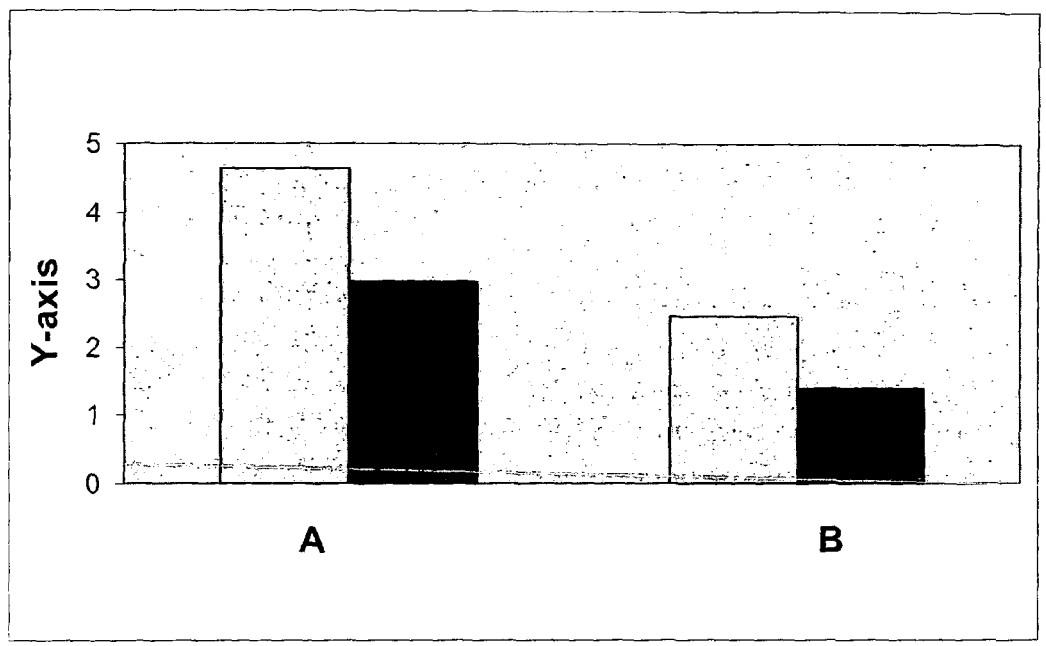

METHOD OF DETERMINATION OF RECEPTOR BINDING SATURATION EFFECTED BY MONOCLONAL ANTIBODIES

CROSS-REFERENCE TO RELATED APPLICATIONS

This application is the U.S. national stage of international patent application PCT/EP2009/004615, filed Jun. 26, 2009, which claims the benefit of and priority to EP Patent Application No. 08013415.8, filed on Jul. 25, 2008.

FIELD OF THE INVENTION

The invention relates to the determination of the degree of membrane receptor binding by specific monoclonal antibodies. This method is notably beneficial for monoclonal antibodies that are used in targeted therapies in order to define a target effective dose (TED). Especially the invention relates to the determination of the saturation degree of receptor binding effected by an anti-EGFR antibody of interest.

BACKGROUND OF THE INVENTION

Drug development is increasingly focusing on targeted therapies directed against membrane receptors. Disruption of signal transduction pathways through pharmacological targeting of relevant membrane receptors has become an effective therapeutic option to is treat e.g. various types of tumors.

Biological molecules, such as monoclonal antibodies (MAbs) as well as small chemical compounds directed against various membrane receptors and other cell proteins on the surface of tumor cells are known to be suitable for anti-tumor therapy for more than twenty years. Mabs specifically bind to their target structures on tumor cells and in most cases also on normal tissues and can cause different effects that dependent on their epitope specificity and/or functional characteristics of the particular antigen. MAbs which bind to an epitope outside the ligand-binding site of membrane receptors (e.g. growth factor receptors with kinase activity) would be expected to induce primarily immune effector functions against the target cell (antibody-dependent cell-mediated cytotoxicity (ADCC), complement-dependent cytotoxicity (CDC)).

MAbs which bind to an epitope within the ligand-binding site or in its direct neighborhood compete for binding of natural ligands to their receptor and thus reduce or completely inhibit ligand binding and can displace already bound ligands from their receptors. This receptor blockade inhibits ligand-dependent receptor activation and downstream signaling.

Membrane tyrosine kinase receptors in tumor cells are a particularly attractive target in anti-tumor therapies. One receptor type tyrosine kinase subfamily, designated as HER or ErbB subfamily, is comprised of EGFR (ErbB1), HER2 (ErbB2 or p185neu), HER3 (ErbB3), and HER4 (ErbB4 or tyro2). Ligands of this subfamily of receptors include epithelial growth factor (EGF), TGF-a, amphiregulin, HB-EGF, betacellulin, heregulin and neuregulins. Among this subfamily the EGFR emerge as one of the most promising targets in anti-tumor therapies.

EGFR is a 170 kD membrane-spanning glycoprotein containing (1) an amino-terminal extracellular domain comprised of 621 amino acid residues, which includes the ligand-binding domain; (2) a single 23-amino-acid transmembrane-anchoring region which may contribute to stability; and (3) a 542-amino-acid carboxyl-terminal intracellular domain which possesses tyrosine kinase activity that activates cytoplasmic targets. Examples of ligands that stimulate EGFR include epidermal growth factor (EGF), transforming growth factor-cc (TGF-a), heparin-binding growth factor (HBGF), (3-cellulin, and Cripto-1. Binding of specific ligands results in EGFR autophosphorylation, activation of the receptor's cytoplasmic tyrosine kinase domain and initiation of multiple signal transduction pathways that regulate tumor growth and survival.

It should be remarked that receptor protein tyrosine kinases, such as EGFR kinase are able to undergo both homo- and heterodimerization, wherein homodimeric receptor combinations are less mitogenic and transforming (no or weak initiation of signaling) than the corresponding heterodimeric combinations (Yarden and Sliwkowski, 2001, Nature Reviews, Molecular cell Biology, volume 2, 127-137; Tzahar and Yarden, 1998, BBA 1377, M25-M37).

Oncogenic transformation due to aberrant EGFR signaling can be a consequence of several different mechanisms, including receptor overexpression.

The epidermal growth factor receptor (EGFR) is aberrantly activated in a variety of epithelial cancers and has been the focus of much interest as a therapeutic target in anti-tumor therapy. EGFR is involved in critical cellular processes such as proliferation, differentiation and apoptosis (Hubbard and Miller, 2007). Misregulation of EGFR, through overexpression or mutation, leads to constitutive activity or impaired receptor downregulation and can cause malignant transformation of the cell (Mendelsohn and Baselga, 2006).

One of the most important strategies to pharmacologically target EGFR, includes monoclonal antibodies (MAbs) which compete with activating EGFR ligands for binding to the ligand-binding side in the extracellular receptor domain.

The first strategy used clinically to target aberrant EGFR signaling in malignant cells was the use of MAbs. Anti-EGFR antibodies not only disrupt receptor/ligand interactions, blocking aberrant signaling and thus tumor cell proliferation and growth, but they may also modulate anti-tumor effectors via antibody-dependent cellular cyto-toxicity (ADCC). Natural killer (NK) cells mediate ADCC by recognizing the carboxyl-terminal ends of antibody molecules via the low-affinity receptor for IgG, FcyRIIIA/CD16. NK cells therefore can closely interact with antibody-coated tumor cells and destroy cells via necrosis and apoptosis.

The first murine anti-EGFR MAb developed showed good anti-tumor activity in animal models. However, their clinical use was limited due to the high incidence of human antimurine antibodies in patients, resulting in reduced efficacy. In response to this disadvantage, researchers developed chimeric and humanized forms of anti-EGFR MAbs.

Cetuximab (IMC-C225, Erbitux©) a chimeric anti-EGFR antibody, was the first Mab of this type that successfully completed clinical trials and was launched in 2003 as a treatment for several cancers. Cetuximab is described e.g. in WO96/40210.

There are a number of other anti-EGFR antibodies under active clinical development for the treatment of cancer. One of them is matuzumab.

Matuzumab (EMD-72000) is a humanized $IgG_1$ MAb that binds with high specificity and affinity to EGFR. Matuzumab is described in WO1992/015683. It has been shown in animal tumor xenograft models to have potent inhibitory activity against human cancers, including head and neck, gastric, pancreatic and lung cancers. Matuzumab was shown to block EGF binding to EGFR, thereby inhibiting downstream signaling pathways, and it may also act via ADCC through FcR binding on immune cells. Matuzumab was selected for further development as a treatment for cancer. Matuzumab exhibited antitumor activity against surgical specimens of EGFR expressing human lung (LXFA629) and gastric (GXF251) adenocarcinomas and pancreas adenosquamous carcinoma (PAXF546) that were insensitive to chemotherapeutic drugs (bleomycin, cisplatin, vindesine, paclitaxei, ifosfamide) and implanted s.c. in nude mice. Treatment with matuzumab (0.5 or 0.5 mg/mouse i.p. once weekly for 2 weeks starting when tumors reached 70-120 mm$^3$) was well tolerated and effective against all 3 tumor types. Complete remissions were observed in 83% and 87%, respectively, of animals bearing gastric and lung carcinomas treated with the higher dose. Marked reductions in pancreatic tumors were observed, such that a mean tumor volume of 31% compared to controls was obtained (27). The anti-tumor efficacy of matuzumab (40 mg/kg biweekly) in mice bearing orthotopic human L3.6pI pancreatic tumors was shown to be enhanced by simultaneous treatment with gemcitabine (100 mg/kg biweekly). Treatment with either agent alone caused a reduction in tumor size and lymph node and liver metastases. These effects were markedly enhanced by combination treatment. Treatment with matuzumab alone or in combination with gemcitabine also significantly decreased microvessel density and proliferative indices. Results from in vitro and in vivo studies further suggest that the anti-tumor effects of matuzumab involve ADCC.

A combination of cetuximab and matuzumab results in a synergistic effect of tumor regression (WO2004/032960).

A combination of anti-EGFR antibodies with chemotherapeutic agents elicits also an enhanced anti-tumor effect (e.g. EP0667165).

Besides Mabs there are numerous small chemical drugs which are known to be potent inhibitors of membrane receptors. Regarding ErbB receptors they block the binding site of the natural ligands, or block the tyrosine residues of the binding site of the receptor kinase, thus preventing phosphorylation and further cascade signaling. One representative showing high efficacy in clinical trials is Iressa™ (ZD-1839) which can be applied for NSCLC indication (non-small cell lung cancer).

In contrast to these conventional cytotoxic drugs, targeted therapies cannot be applied at the maximum tolerated dose (MTD) since it may interact with other signal pathways if administered in supra saturating doses. In oncology or hematology targeted therapies are combined with these cytotoxic drugs frequently. The combination therapies of targeted drugs may influence safety profile. This problem leads to the need for a dose reduction of the MAbs. Thus, a target effective dose (TED) has to be defined to ensure a sufficient MAb dosing. The assessment of receptor binding saturation significantly contributes to the definition of a dose rationale i.e. the TED and is superior to investigate effectiveness on downstream signaling that may be altered by salvage pathways.

SUMMARY OF THE INVENTION

According to the state of the art MAbs are administered to patients or stand in clinical trial to treat disorders such us different types of cancer. In these targeted therapies determination of TED mainly depends on the saturation of the target tissue effected by the therapeutic MAb. Using the known detection methods like immunohistochemistry it is impossible to measure the grade of saturation.

There are different hints that forbid the determination of the degree of receptor binding saturation in a direct way:
(1) To make the saturation comparable to conditions under therapy it is not possible to administer labeled antibody. Labeling markers coupled to therapeutic Mabs such as a fluorescence dye i.e. FITC or the nuclear medicine imaging isomer Tc-99m or molecules such as biotin would allow the determination of receptor binding saturation by means of a target tissue biopsie. However, use of labeled antibodies is not suitable under therapy.
(2) Mostly it is difficult or even not possible to obtain a biopsie of the target tissue for medical reasons.

For these reasons determination of TED in a reliable way is necessary and overdue.

The invention relates to the etablisment of an immunehistochemical assay which allows to determine the degree of membrane receptor domains identified by an specific epitope E1 which is bound by a Mab of interest which is herein named monoclonal Ab1. Especially, the invention relates to a method which enables the detection of receptor binding saturation by means of ex vivo tissue samples treated by monoclonal Ab1.

In an other aspect of this invention, the use of a surrogate tissue was shown to suit for the determination of receptor binding saturation in case biopsies of target tissues are not obtainable.

The immunohistochemical assay includes (during or after the application of antibody Ab1 which specifically binds to an epitope (E1) of a receptor domain in a tissue sample):
   (i) the application of a first antibody Ab1A which recognizes and binds to the same but unsaturated epitope E1 of the receptor domain in a tissue sample, and
   (ii) the application of a second antibody Ab2 which binds to an epitope (E2) of the same receptor domain in the tissue sample of (i) representing the whole amount of the receptor domain.

Comparing these results the receptor domain binding of the antibody of interest Ab1 can be calculated in a semiquantitative manner. Since monoclonal antibodies are used in targeted therapies directed against receptor domains this method is beneficial for the determination of a target effective dose (TED).

Mabs administered to treat diseases such as cancer have increasingly human origin or are humanized. The determination of receptor binding saturation in patient tissue samples ex vivo requires a non-humanized or non-human monoclonal Ab1A, that detects exactly the same epitope as the therapeutic humanized or human Ab1. Because of the non-human source of antibody Ab1A it is possible to detect the unoccupied target epitope i.e. in the receptor domain. The application of such an antibody enables to detect the unoccupied target epitope ex vivo in tissue samples taken during or after treatment with the therapeutic antibody.

If Ab1A would be a human or humanized Mab such as the therapeutic antibody an individual detection system for Ab1 and Ab1A could not be provided. An individual detection system is a prerequisite of the immunehistochemical assay fo this invention to evaluate the unique staining effected by Ab1 and Ab1A.

By usage of another non-human antibody Ab2 directed against the receptor domain but a different epitope on this protein it is possible using certain immunohistochemical techniques to determine the whole amount of the protein. Comparing these findings with the results of the application of Ab1A it is possible to determine the ratio between the targets occupied by the therapeutic antibody Ab1 and the whole amount of the receptor.

In a preferred embodiment, a patient is treated with a therapeutic monoclonal antibody Ab1 against a tumor. During the course of treatment or after the treatment at a point of time to be determined a tissue sample (for example a tumor or another tissue sample which contains the target receptor domain) is taken and stored for example by immediate snap freezing. The tissue sample has to express the receptor to which the antibodies Ab1 and Ab1A bind. This may be a diseased tissue, a tumor tissue or simply, if possible, skin tissue. A section of the tissue sample is incubated with Ab1A which detects exactly the same epitope as the therapeutic antibody. Preferably, Ab1 and Ab1A have the same or a similar binding affinity to epitope E1. According to the invention, Ab1A may be the same antibody as Ab1 or a murine, chimeric or humanized version thereof recognizing the same epitope E1 but is coupled to an unique detection system. Preferably Ab1A is identical with Ab1.

In parallel, an equivalent section of the tissue sample is incubated with an non-human antibody Ab2 (preferably murine or rat) directed against the receptor domain but a different epitope E2 on the receptor wherein this antibody is coupled to an unique detection system. By usage of Ab2 it is possible to determine the whole amount of the protein. Receptor binding saturation is determined as the ratio of receptor domains detected by the competing Mab 1A and receptors domains detected by the control Mab 2. It is important according to the invention that epitope E2 or its binding pocket on the same receptor is located in a distance to epitope E1 (or its binding pocket) which is far enough that no or no significant interactions between antibodies binding to E1 and E2 may occur. In other words binding of Ab2 to E2 shall not influenced by binding of Ab1 or Ab1A to E1 and vice versa.

In another aspect of this invention, Ab1A has the same heavy and light chain sequences as Ab1. Consequently, Ab1A detects the same epitope of the receptor domain as therapeutic Ab1. Additionally, Ab1A is labelled by a individual unique detection system which allows to detect the Ab1A-receptor domain binding. The application of such an antibody enables to detect unoccupied target proteins ex vivo in tissue samples taken during or after treatment with the therapeutic antibody.

By usage of another non-human antibody Ab2 directed against the receptor domain but a different epitope on this protein it is possible using certain immunohistochemical techniques to determine the whole amount of the protein. Comparing these findings with the results from the application of Ab1A it is possible to determine the ratio between the targets occupied by the therapeutic antibody Ab1 and the whole amount of the receptor. The use of Ab1A having the same heavy and light chain sequences as Ab1 provides the identical binding affinity in comparison to the therapeutic A1. The use of such conditions makes the immunehistochemical assay of this invention highly reliable.

In a preferred embodiment, a patient is treated with a therapeutic monoclonal antibody Ab1 against a tumor. During the course of treatment or after the treatment at a point of time to be determined a tissue sample (a tumor or another tissue sample which contains the target receptor domain) is taken and immediately snap frozen. A section of the tissue sample is incubated with Ab1A which has the same heavy and light chain sequences as Ab1 and is labelled by a individual unique detection system which allows to detect the Ab1A-receptor domain binding. In parallel, a section of the tissue sample is incubated with Ab2 directed against the receptor domain but a different epitope on this protein wherein this antibody is coupled to an unique detection system. By usage of Ab2 it is possible to determine the whole amount of the protein. Receptor binding saturation is determined as the ratio of receptor domains detected by the competing Mab 1A and receptors domains detected by the control Mab 2.

In one embodiment of the invention antibody Ab1 is directed against a specific epitope E1 of the EGF receptor. In a preferred embodiment Ab1 is an anti-EGFR antibody selected from antibodies matuzumab (EMD72000, hMab425) or cetuximab (Erbitux, c225) which binds to different epitopes E1 (E1A/E1b) of the EGFR. In this case Ab1A may be also matuzumab (or cetuximab) which is provided with a unique detection marker or the murine or a chimeric version thereof coupled to an unique detection marker.

In a notably preferred embodiment, a patient is treated with the therapeutic Mab EMD72000. During the course of treatment or after the treatment at a point of time to be determined a tumor or skin tissue sample which contains the target EGFR is taken and for example immediately snap frozen. A section of a tissue sample (skin, tumor etc.) is incubated with a biotinylated EMD72000 that was additionally labeled with biotin. By usage for example of the mouse IgG1-antibody E62 which is directed against a epitope E2 of the EGF-receptor domain, it is possible by using certain immunohistochemical techniques to determine the whole amount of the protein. Receptor binding saturation is determined as the ratio of receptor domains detected by the competing biotinylated EMD72000 and receptors domains detected by the control mAb E62. Antibody is known from (European Archives of Oto-Rhino-Laryngology 1995, 252, 433-439). There are other anti-EGFR antibodies which are known to bind epitopes E2 in a distance far enough from the epitopes E1 to which EMD72000 or cetuximab binds.

In a further embodiment, a patient is treated with the therapeutic Mab EMD72000 (matuzumab). During the course of treatment or after the treatment at a point of time to be determined a tissue sample, for example from tumor or skin which expresses the EGF receptor is taken. A section of the preferably snap frozen tissue sample is incubated with the monoclonal antibody EMD59000. EMD59000 is a murine Mab of isotype IgG2a which recognizes the same epitope in the EGFR as EMD72000. In parallel, a section of the tissue sample is incubated with the mouse IgG1-antibody E62 directed against a different epitope E2 of the receptor domain wherein the antibody is coupled to an unique detection system. By usage of mAb E62 it is possible using certain immunohistochemical techniques to determine the whole amount of the protein. Receptor binding saturation is determined as the ratio of receptor domains detected by the competing EMD55900 and receptors domains detected by the control mAb E62.

In another aspect of this invention, the degree of receptor binding saturation effected by a further diagnostic antibody of interest (Ab1A) could be determined by the immunohistochemical assay of this invention. The immunohistochemical assay includes (during or after the application of antibody Ab1 which specifically binds to an epitope (E1) of a receptor domain in a tissue sample):

the application of an Ab1A which recognizes and binds to the same but unsaturated epitope E1 of the receptor domain in an tissue sample, and the application of an Ab2 which binds to an epitope (E2) of the same receptor domain in a tissue sample representing the whole amount of the receptor domain.

Using these results the receptor domain binding can be calculated in a semiquantitative manner.

Thus, the invention relates in more detail to the following:

A method for determining the degree of receptor binding saturation effected by a monoclonal antibody of interest (Ab1) by means of a first (Ab1A) and a second (Ab2) monoclonal antibody each provided with an individual detection system, wherein Ab1 specifically binds to an epitope (E1) of a receptor domain in a tissue sample, Ab1A recognizes and binds to the same epitope E1 of the receptor domain, and Ab2 binds to an epitope (E2) of the same receptor domain that is different from E1, and said binding of Ab2 does not interact with binding of Ab1 or Ab1A to E1, the method comprising the steps: (i) applying antibody Ab2 to a tissue sample of an individual in an amount which is sufficient to achieve receptor binding saturation towards E2 and determining the signal strength provided by the individual detection system associated with antibody Ab2, (ii) applying antibody Ab1A to a tissue sample of the same individual that was treated before with said antibody Ab1, in an amount which is sufficient to bind to receptor epitope E1 not already bound by antibody Ab1, and determining the signal strength provided by the individual detection system associated with antibody Ab1A, and (iii) calculating from the difference of the signal strength obtained by steps (i) and (ii), the amount of receptor domains which can still bind antibody Ab1, thus determining the degree of receptor binding saturation effected by antibody Ab1.

A method as defined above comprising as initial step adjusting the signal strength provided by the individual detection system associated with antibody Ab2 to the signal strength provided by the individual detection system associated with antibody Ab1a, wherein Ab2 and Ab1a have been applied to any tissue sample from the same source but not treated with antibody Ab1.

A method as defined above, wherein the binding affinity of antibody Ab1 to epitope E1 is identical or similar to that of antibody Ab1A to E1.

A method as defined above, wherein the binding affinity of antibody Ab2 to epitope E2 is identical or similar to that of antibody Ab1 to epitope E1.

A method as defined above, wherein the individual detection system unique detection marker associated with antibody Ab2 and antibody Ab1A is a detection marker, and exploiting of the signal strength generated is done in a semi-quantitative manner.

A method as defined above, wherein the detection marker is a dye.

A method as defined above, wherein antibody Ab1 and antibody Ab1A have the same heavy and light chain sequences.

A method as defined above, wherein the receptor domain is a tyrosine kinase membrane receptor selected from the group consisting of EGFR (Her1, ErbB1), Her2 (ErbB2) and Her3 (ErbB3), and antibodies Ab1, Ab2 and Ab1A are antibodies directed to at least one of these receptors.

A method as defined above, wherein antibody Ab1 is matuzumab (Mab h425) or cetuximab (Mab c225, Erbitux®) or a binding-active fragment/derivative or a respective murine, chimeric or humanized version thereof.

A method as defined above, wherein the tissue sample from said individual is from skin tissue.

A method as defined above, wherein the receptor pattern and profile of the skin tissue is related to the receptor pattern and profile of tumor tissue in said individual.

A method as defined above, wherein said tissue sample derives from an individual suffering from cancer or a respective disease or disorder.

A method as defined above, wherein antibody Ab1 is a therapeutic antibody.

A method as defined above, wherein antibody Ab1 is a human or humanized or chimeric antibody and antibody Ab2 is a mouse or rat antibody.

Use of a method as defined above for finding and optimizing ex vivo an effective dose of an antibody suitable for application in a therapy, especially an anti-tumor therapy.

An ex vivo-method of finding and optimizing an effective dose of a therapeutic antibody of interest, which is administered to a patient, comprising a method as specified in any of the claims 1-14, optionally followed by repeating at least one time steps (i) to (iii) after an altered dose of antibody Ab1 has been administered to the patient, until saturation of the receptor with antibody Ab1 can be measured and the optimum individual effective dose for said patient is found.

A method as defined above, wherein the finding of optimum receptor saturation is used to avoid underdosing or overdosing of the therapeutic antibody.

A diagnostic kit comprising (i) a first package containing a therapeutic monoclonal antibody (Ab1), (ii) a second package containing a first diagnostic monoclonal antibody (Ab1A) associated with an individual detection system, and (iii) a third package containing a second diagnostic monoclonal antibody (Ab2) associated with an individual detection system, wherein antibody Ab1 specifically binds to an epitope (E1) of a ligand-receptor domain in a tissue sample, Ab1A recognizes and binds to the same epitope E1 of the receptor domain, and Ab2 binds to an epitope (E2) of the same receptor domain that is different from E1, and said binding of Ab2 does not interact with binding of Ab1 or Ab1A to E1.

Use of a diagnostic kit as defined above for finding ex vivo an effective and optimum individual dose of a therapeutic antibody in a patient.

DETAILED DESCRIPTION OF THE INVENTION

A prerequisite for the appliance of the immunehistochemical assay of this invention is an initial step comprising the adjustment of the signal strength provided by the individual detection system associated with antibody Ab2 to the signal strength provided by the individual detection system associated with antibody Ab1a, wherein Ab2 and Ab1a have been applied to any tissue sample from the same source but not treated with antibody Ab1.

In a preferred embodiment, the concentrations of the antibody Ab2 (e.g. mAb E62 and the biotinylated EMD72000 antibodies were adjusted so that samples of untreated to human skin exhibited the same staining intensity and distribution in the tissue sample.

Although the immunehistochemical assay of this invention was described above for the EGFR as target receptor molecules only it should be pointed out that the scientific principle discovered by the inventors and stated above and below might also applicable for other biological receptors besides EGFR.

The immunohistochemical assay of this invention as specified herein and in the claim 16 can be used for the finding and optimizing of an effective dose of an therapeutic used preferably in an anti-tumour therapy. A benefit of lowering the dose of the compounds, compositions, agents and therapies administered to an individual includes a decrease in the incidence of adverse effects associated with higher dosages. For example, by the lowering the dosage of an agent described above and below, a reduction in the frequency and the severity of nausea and vomiting will result when compared to that observed at higher dosages. By lowering the incidence of adverse effects, an improvement in the quality of life of a cancer patient is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

The immunohistochemical assay of this invention allows the determination of the target effective dose for every individual patient. This method is applicable in the case of every patient if a tumor tissue sample or a surrogate tissue sample is available. Optimization of the therapeutic effective dose to every patient is important since e.g. pharmakodynamic and/or pharmacokinetic properties of therapeutic agents are unique to every patient.

According to this invention an "individual detection system" means that a staining of an antibody is coupled to a detection system that is unique and can precisely differentiated from other stainings effected by other antibodies.

Individual detection system means as well several steps can be coupled to the application of the antibody in order to make the staining detectable. For example, antibody Ab1A or Ab2 can be labeled via molecules e.g. biotin, a biotin-avidin complex or a biotin-streptavidin complex and a second antibody directed against the labeling molecule is applied. The second antibody is coupled to a dye or an enzyme. The used dyes are preferably but not limited fluorescence, chromogenic or luminescence dyes. The used enzymes convert a substrat which results e.g. in a chromogenic or fluorescence or luminescence signal. The last step in the individual detection system which makes the staining of the antibody detectable is defined as the detection marker.

In a preferred embodiment of this invention, an anti-biotin-antibody directed against the biotylinated Ab1a e.g. EMD72000 is labeled to peroxidase. The peroxidase elicits a signal by converting the chromogenic substrat diaminobenzidine (=DAB).

In addition, a secondary antibody can be applied which recognizes the Fc-region of antibody 1a or 2. In addition, the antibody directed against Ab1A or Ab2 can be labeled via molecules e.g. biotin or a biotin-avidin complex.

In addition, labeling complexes such as biotin-avidin can be directly coupled to enzymes that elicit a signal by converting a substrat. Such biotin-avidin complexes are called ABC.

In addition, linkers may be used between the labels and the antibodies in the individual detection system.

Although above-individual detection system are described for antibodies also binding-active fragments/derivatives or a respective murine, chimeric or humanized version thereof are included.

The term "signal strength" used in the context of this invention means that the intensity of the signal produced by antibody Ab1A and Ab2 in the specific staining reactions should be adjusted optimally, preferably in untreated tissue sample. The adjustement is reached e.g. by different dilutions of antibodies and/or reagents in this assay. An equivalent signal strength, preferably in this invention effected by the biotinylated antibodies such as EMD 72000 and E62, is a prerequisite of this assay. The exploiting of the signal strength is done in a semiquantitative manner. In a preferred embodiment of this invention, the signal strength is evaluated via an IRS-score (=immune reactive score, see example 1).

A "tissue sample" means a biopsie that is removed from an individual in order to use this material, preferably in terms of sections, for the immunohistochemical assay of this invention. Preferably to this invention skin and/or tumours samples are used.

A "receptor" or "receptor molecule" is a soluble or membrane bound/associated protein or glycoprotein comprising one or more domains to which a ligand binds to form a receptor-ligand complex. By binding the ligand, which may be an agonist or an antagonist the receptor is activated or inactivated and may initiate or block pathway signaling.

A "ligand" or "receptor ligand" is meant a natural or synthetic compound or in the context of this invention an monoclonal antibody which binds a receptor molecule to form a receptor-ligand complex. The term ligand includes agonists, antagonists, and compounds with partial agonist/antagonist action.

A "receptor domain" is a part of the receptor molecule that forms a special three-dimensional structure in the molecule. A "receptor domain" is in the context of this invention the local region (binding sequence/loop/pocket) of the receptor to which a natural ligand or an antibody or an drug binds. This region may comprise not only one specific epitope but two or more epitopes, respectively. According to thi invention, a specific antibody binds to a specific epitope within the receptor domain.

The term "degree or grade of receptor binding saturation" means the procentual portion of receptors (on the cells contained in the investigated tissue sample) that are bound by the monoclonal antibody 1.

The term "receptor pattern of an tissue" relates to the density of receptors/integrated to the surface of on cell type and/or other cell types building the tissue. "The profile of an tissue" relates e.g. to the number of cell types and/or their distribution and/or their morphological forms and/or their conditions. In a preferred embodiment of this invention, the receptor pattern and the profile in the tumour tissue and in the skin tissue should be similar since skin tissue is treated as a reliable surrogate tissue for a tumour biopsie.

A "similar binding affinity" between the antibodies Ab1 and Ab1A to epitope 1 according to the invention means that the antibodies do not differ in their binding affinity more than 30%, preferably not more than 20% and most preferably not more than 10%.

A "similar binding affinity" between the antibodies Ab1A to epitope 1 and Ab2 to epitope 2 means that the antibodies do not differ in their binding affinity more than 30%, preferably not more than 20% and most preferably not more than 10%.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. Methods for making monoclonal antibodies include the hybridoma method described by Kohler and Milstein (1975, Nature 256, 495) and in "Monoclonal Antibody Technology, The Production and Characterization of Rodent and Human Hybridomas" (1985, Burdon et al., Eds, Laboratory Techniques in Biochemistry and Molecular Biology, Volume 13, Elsevier Science Publishers, Amsterdam), or may be made by well known recombinant DNA methods (see, e.g., U.S. Pat. No. 4,816,567). Monoclonal antibodies may also be isolated from phage antibody libraries using the techniques described in Clackson et al., *Nature,* 352:624-628 (1991) and Marks et al., *J. Mol. Biol.,* 222:58, 1-597 (1991), for example.

The term "chimeric antibody" means antibodies in which a portion of the heavy and/or light chain is identical with or homologous to corresponding sequences in antibodies derived from a particular species or belonging to a particular antibody class or subclass, while the remainder of the chain(s)

is identical with or homologous to corresponding sequences in antibodies derived from another species or belonging to another antibody class or subclass, as well as fragments of such antibodies, so long as they exhibit the desired biological activity (e.g.: U.S. Pat. No. 4,816,567; Morrison et al., *Proc. Nat. Acad. Sci. USA*, 81:6851-6855 (1984)). Methods for making chimeric and humanized antibodies are also known in the art. For example, methods for making chimeric antibodies include those described in patents by Boss (Celltech) and by Cabilly (Genentech) (U.S. Pat. No. 4,816,397; U.S. Pat. No. 4,816,567).

"Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody.

These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

"Human antibodies" are antibodies comprising completely human sequences.

"Murine antibodies" are antibodies that contain murine sequences by the majority.

A "Binding active fragment" comprise a portion of an intact antibody, namely the antigen-binding or variable region thereof. Examples of antibody fragments include Fab, Fab', F(ab')2, Fv, diabodies, linear antibodies, single-chain antibody molecules; and multispecific antibodies formed from antibody fragment(s).

A "derivative" represents a deduced form of an antibody.

Murine, chimeric or humanized versions of an antibody in the context of this invention include equivalent antibodies or derivatives wherein portions of antibody are substituted according to the definitions of murine antibodies, chimeric antibodies or humanized antibodies.

A "therapeutic antibody" in the context of this invention relates to an antibody that is directed against a specific epitope of a receptor domain and therefore can be used as a therapeutic reagent to treat a disease or disorder. In a preferred embodiment of this invention therapeutic antibodies are used in anti-cancer therapies.

A "diagnostic antibody" in the context of this invention relates to an antibody that is directed against a specific epitope of a receptor domain and therefore can be used as a diagnostic tool.

The terms "cancer" and "tumor" refer to or describe the physiological condition in mammals that is typically characterized by unregulated cell growth. By means of the pharmaceutical compositions according of the present invention tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

The term "cytotoxic drug" means a "chemotherapeutic agent" i.e. specifically chemical agents that exert anti-neoplastic effects, preferably directly on the tumor cell, and less indirectly through mechanisms such as biological response modification. Suitable chemotherapeutic agents according to the invention are preferably natural or synthetic chemical compounds. There are large numbers of anti-neoplastic chemical agents available in commercial use, in clinical evaluation and in pre-clinical development, which could be included in the present invention for treatment of tumors/neoplasia by combination therapy with the receptor antagonists as claimed and described in this invention. It should be pointed out that the chemotherapeutic agents can be administered optionally together with said ErbB receptor antagonists.

Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; cytotoxic antibiotics and camptothecin derivatives.

Most preferred chemotherapeutic agents according to the invention are cisplatin, gemcitabine, doxorubicin, paclitaxel (taxol) and bleomycin.

A "maximum tolerated dose=MTD" means the highest dose of a drug or treatment that does not cause unacceptable side effects. The maximum tolerated dose is determined in clinical trials by testing increasing doses on different groups of people until the highest dose with acceptable side effects is found.

A "supra saturating dose" is far beyond the MTD

"Overdosing" means to administer too large a dose or to many doses to a patient. Overdosing is associated with the incidence of adverse effects. For example, overdosing is connected with nausea and vomiting.

"Underdosing" means to administer too small a dose or to less doses. Underdosing erodes at efficacy of the therapy. Underdosing as well as overdosing will result in a decrease in net treatment benefit.

The term "therapeutically effective dose=TED" refers to an amount of a drug e.g. therapeutic antibody effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For anti-tumour therapy, efficacy can, for example, be measured by assessing the time to disease progression (TTP) and/or determining the response rate (RR).

The term "diagnostic kit" for determination of receptor binding saturation includes different packages of diagnostic and therapeutic antibodies and reagents which are necessary for the application of the immunohistochemical assay of this invention and, as a rule, instructions for using the reagents and antibodies. The antibodies as well as the reagent can be provided as a liquid, powder, tablet, suspension. The antibodies and reagents may be provided in separate packages suitable for application separately according to the present method. A kit of this invention also contains "instruction for use" of the materials contained in the package.

In summary, a diagnostic kit according to the present invention preferably comprises the following combinations:
(i) the therapeutic antibody Ab1 (e.g. EMD72000 or cetuximab)
(ii) the first diagnostic Mab Ab1A which preferably has the same heavy and light chain sequences as Ab1 but is additionally labeled by biotin.
(iii) Antibody Ab2 (e.g. the mouse IgG1-antibody E62) directed against a different epitope E2 of the receptor domain.

FIG. 1: Comparison of Corresponding Patient Samples

Figure 1B:
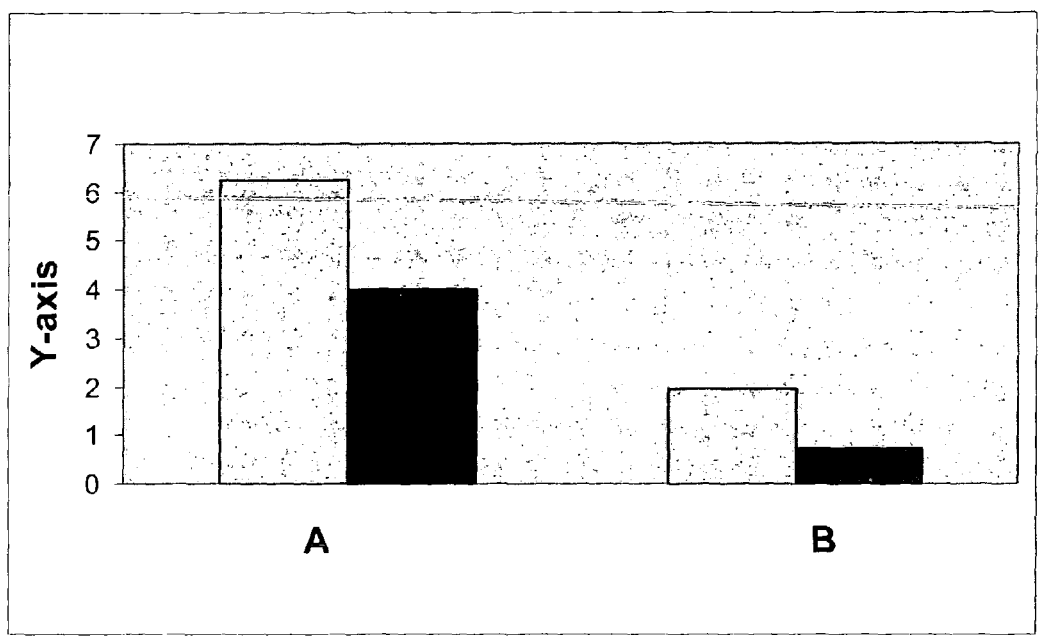

Mean IRS values (y-axis) of all skin (A) and tumor (B) tissue sample stained with the antibody E 62 (left column in A and B) and biotinylated antibody EMD 72000 (right column in A and B) and taken after study Phase A (FIG. 1a) and Phase B (FIG. 1b).

EXAMPLE 1

In a Phase I study saturation of EGFR effected by intravenous administered antibody EMD 72000 was investigated.

Therefore, an immune histochemical assay with two several antibodies was employed. Murine antibody E 62 (manufactured and provided by Merck KGaA, Darmstadt) binds to an epitope of the extracellular domain of the EGFR which is different from the binding site of natural ligands and the specific antibody EMD72000. The staining with E 62 displays the whole content of EGF receptor per cell/tissue sample. Biotinylated antibody EMD 72000 (manufactured and provided by Merck KGaA, Darmstadt) is a variant of the therapeutic EMD 72000 sharing the same binding site at the extracellular domain of the EGF receptor with the natural ligands (e.g. EGF and TGFalpha).

EGF receptor blockade or even receptor binding saturation achieved by in vivo or in vitro administration of EMD 72000 should reduce or eliminate the staining effected by the biotinylated EMD 72000 antibody in comparison to the staining of E62. The staining was evaluated by two autonomous pathologists using a semiquantitative immune reactive score (IRS-score). These results were investigated for statistical significance.

Skin and tumour tissue samples from patients with oesophago-gastric cancer treated with the therapeutic antibody EMD 72000 in combination with the chemotherapeutic drug combination ECX (comprising epirubicin, cisplatin and capecitabine) were investigated in this study. Tested in different clinical studies with several cancer types a therapeutic potency of EMD 72000 alone or in combination with radiation or other chemotherapeutics resulting in tumor size reduction, stable disease or even tumor regression has been demonstrated.

The assay was validated at a xenograft tumor model after intravenous administration of EMD 72000 in nude mice. Thereby a partial EGF receptor blockade in three different cancer types due to administration of EMD 72000 in comparison to the untreated control group was shown respectively.

The goal was to determine if skin is a reliable surrogate tissue to verify EGFR blockade or saturation by the therapeutic antibody EMD 72000 and to compare EGFR blockade in skin and tumor.

Materials and Methods

Skin and tumor tissue samples of different patients were investigated. Tumor tissue of the patients were taken at different time points, the first at the end of the $2^{nd}$ cycle of treatment with EMD72000 (after 6 weeks)=Phase A and the second at the end of the $4^{th}$ cycle (after 12 weeks)=Phase B.

In a first step of our investigations cryo sections of all tumor samples were stained with Hematoxilin/Eosin to analyze the content of tumor cells. Tumor samples which comprise more than 500 vital tumor cells were analyzed.

Cryosections

Shock frozen tumor and skin tissue samples were cut in 5 μm sections. From each tissue sample two microscope slides with 5 tissue sections at each were prepared. One microscope slide was stained with the mAb E62 and the second slide with the biotinylated antibody EMD 72000, both in the same staining run.

Immunohistochemical Stainings

The staining with E 62 displays the full amount of EGF receptor of the tissue sections. The biotinylated antibody EMD 72000 is a variant of the therapeutic monoclonal humanized antibody EMD 72000 with the same binding site at the extra cellular matrix of the EGF receptor. All tissue samples (skin and tumor) of one single patient were stained in the same run due to avoid different staining conditions (e.g. room temperature). At each staining run a positive and negative control slight with a tissue sample of untreated human skin were taken along.

The antibody concentrations of E 62 and the biotinylated EMD 72000 must be adjusted in such a way that samples of untreated human skin exhibit the same intensity and distribution of staining with both antibodies.

Methods of Evaluation and Statistics

The evaluation of the two several antibody stainings was performed if at each microscopic slight at least 3 sections were evaluable. The analysis of immunohistochemical stainings with antibody E 62 and biotinylated EMD 72000 was performed by two autonomous pathologists using a light microscope.

The IRS score is a semi-quantitative system which incorporates the staining intensity and the percentage of positive cells. The factor for intensity (0-3) is multiplied by the factor of percentage (1-4) so that the maximum of the IRS score is 12 which is expressed in a strong staining (score 3) of more than 80% epidermal or vital tumor cells, for example. In the best manner for statistical analysis there were five IRS values obtained per tissue sample and per immunohistochemical staining. The IRS scores were averaged over the tissue sections and assessed by a Wilcoxon rank sum test.

Results

Regarding the mean IRS values of skin and tumor both tissue species exhibit similar results in staining with the mAb E62 and biotinylated EMD 72000 after treatment with EMD 72000. So the skin is suitable as a surrogate tissue to confirm the binding of the therapeutic EMD 72000. A significant reduction of colouring with the biotinylated EMD 72000 in comparison with that of mAb E62 of all skin and all tumor samples after Phase A and Phase B was demonstrated. These results approve the function of the employed immune histological assay.

The invention claimed is:

1. A method for determining the degree of receptor binding saturation effected by a monoclonal antibody of interest (Ab1) by means of a first (Ab1A) and a second (Ab2) monoclonal antibody each provided with an individual detection system, wherein Ab1 specifically binds to an epitope (E1) of a receptor domain in a tissue sample, Ab1A recognizes and binds to the same epitope E1 of the receptor domain, and Ab2 binds to an epitope (E2) of the same receptor domain that is different from E1, and said binding of Ab2 does not interact with binding of Ab1 or Ab1A to E1, the method comprising the steps:
- (i) applying antibody Ab2 to a tissue sample of an individual in an amount which is sufficient to achieve receptor binding saturation towards E2 and determining the signal strength provided by the individual detection system associated with antibody Ab2,
- (ii) applying antibody Ab1A to a tissue sample of the same individual that was treated before with said antibody Ab1, in an amount which is sufficient to bind to receptor epitope E1 not already bound by antibody Ab1, and determining the signal strength provided by the individual detection system associated with antibody Ab1A, and
- (iii) calculating from the difference of the signal strength obtained by steps (i) and (ii), the amount of receptor domains which can still bind antibody Ab1, thus determining the degree of receptor binding saturation effected by antibody Ab1.

2. The method of claim 1, comprising as initial step adjusting the signal strength provided by the individual detection system associated with antibody Ab2 to the signal strength provided by the individual detection system associated with antibody Ab1A, wherein Ab2 and Ab1A have been applied to any tissue sample from the same source but not treated with antibody Ab1.

3. The method of claim 1, wherein the binding affinity of antibody Ab1 to epitope E1 is identical or similar to that of antibody Ab1A to E1.

4. The method of claim 1, wherein the binding affinity of antibody Ab2 to epitope E2 is identical or similar to that of antibody Ab1 to epitope E1.

5. The method of claim 1, wherein the individual detection system unique detection marker associated with antibody Ab2 and antibody Ab1A is a detection marker, and exploiting of the signal strength generated is done in a semi-quantitative manner.

6. The method of claim 5, wherein the detection marker is a dye.

7. The method of claim 1, wherein antibody Ab1 and antibody Ab1A have the same heavy and light chain sequences.

8. The method of claim 1, wherein the receptor domain is a tyrosine kinase membrane receptor selected from the group consisting of EGFR (Her1, ErbB1), Her2 (ErbB2) and Her3 (ErbB3), and antibodies Ab1, Ab2 and Ab1A are antibodies directed to at least one of these receptors.

9. The method of claim 8, wherein antibody Ab1 is matuzumab (Mab h425) or cetuximab (Mab c225, Erbitux®) or a binding-active fragment/derivative or a respective murine, chimeric or humanized version thereof.

10. The method of claim 8, wherein the tissue sample from said individual is from skin tissue.

11. The method of claim 10, wherein the receptor pattern and profile of the skin tissue is related to the receptor pattern and profile of tumor tissue in said individual.

12. The method of claim 10, wherein said tissue sample derives from an individual suffering from cancer or a respective disease or disorder.

13. The method of claim 1, wherein antibody Ab1 is a therapeutic antibody.

14. The method of claim 1, wherein antibody Ab1 is a human or humanized or chimeric antibody and antibody Ab2 is a mouse or rat antibody.

15. The method of claim 1, wherein the method is used for finding and optimizing ex vivo an effective dose of an antibody suitable for application in a therapy, especially an anti-tumor therapy.

16. An ex vivo-method of finding and optimizing an effective dose of a therapeutic antibody of interest, which is administered to a patient, comprising the method of claim 1, optionally followed by repeating at least one time steps (i) to (iii) after an altered dose of antibody Ab1 has been administered to the patient, until saturation of the receptor with antibody Ab1 can be measured and the optimum individual effective dose for said patient is found.

17. The method of claim 16, wherein the finding of optimum receptor saturation is used to avoid underdosing or overdosing of the therapeutic antibody.

* * * * *